(12) United States Patent
Sowell et al.

(10) Patent No.: US 6,981,400 B1
(45) Date of Patent: Jan. 3, 2006

(54) SLIP METER FOR DETERMINATION OF SURFACE SLIP RESISTANCE

(75) Inventors: Dale A. Sowell, Alexandria, VA (US); Erick O. Satchell, Waldorf, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 66 days.

(21) Appl. No.: 10/807,576

(22) Filed: Mar. 23, 2004

(51) Int. Cl.
*G01N 19/02* (2006.01)
(52) U.S. Cl. ............................................. 73/9
(58) Field of Classification Search ............ 73/9, 73/763, 774, 781, 788
See application file for complete search history.

(56) References Cited

U.S. PATENT DOCUMENTS

| | | | | |
|---|---|---|---|---|
| 4,315,426 A | * | 2/1982 | Brandon | 73/9 |
| 4,798,080 A | | 1/1989 | Brungraber | |
| 5,259,236 A | | 11/1993 | English | |
| 5,689,058 A | * | 11/1997 | Yuan | 73/9 |
| 5,736,630 A | * | 4/1998 | Welner | 73/9 |
| 6,813,960 B1 | * | 11/2004 | Nagy et al. | 73/808 |

* cited by examiner

*Primary Examiner*—Charles Garber
(74) *Attorney, Agent, or Firm*—Jacob Shuster

(57) ABSTRACT

A slip resistance measuring device features a magnetic actuator pivotally mounted on a portable frame positioned on a test surface to apply a linear force to a test specimen for engagement with the test surface at a preselected inclination angle thereto. The linear force is applied to the test specimen through a strain gauge plate which thereby undergoes stress sensed by a load cell mounted thereon from which strain stress signals are delivered under automatic testing operation to provide slip resistance measurement data for the test surface.

4 Claims, 2 Drawing Sheets

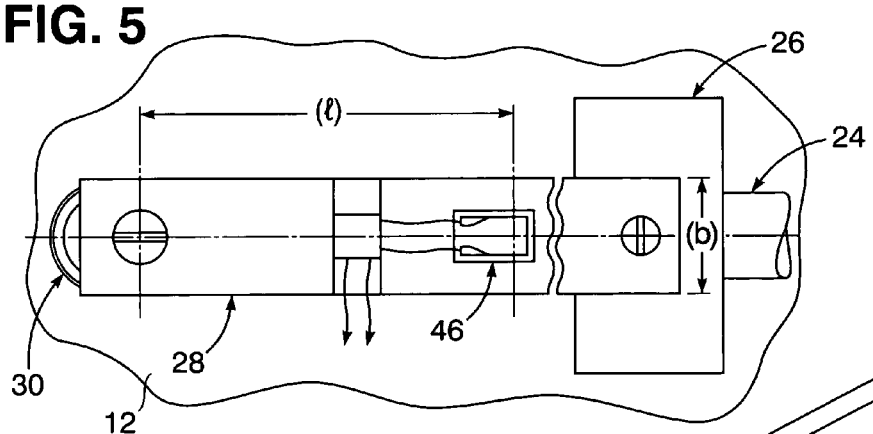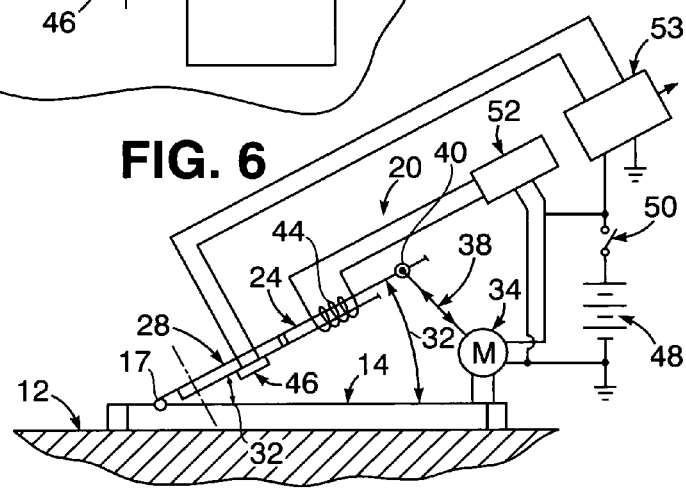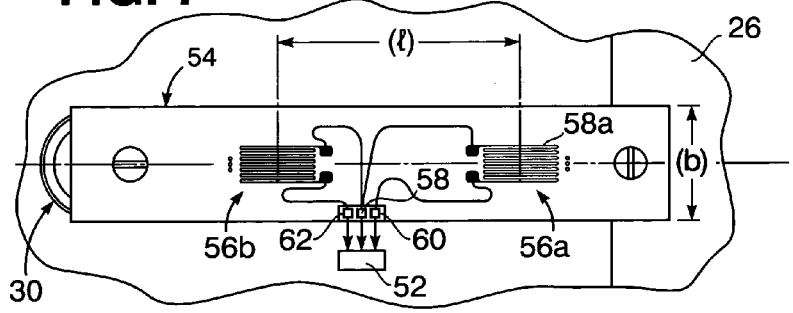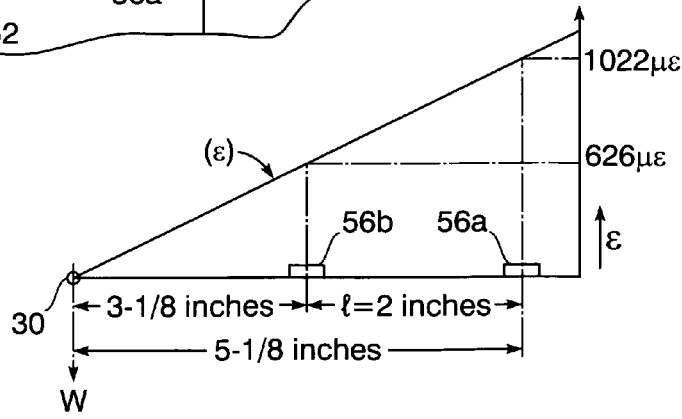

SLIP METER FOR DETERMINATION OF SURFACE SLIP RESISTANCE

STATEMENT OF GOVERNMENT INTEREST

The invention described herein may be manufactured and used by or for the Government of the United States of America for governmental purposes without the payment of any royalties thereon or therefore.

The present invention relates to the measurement of slip resistance on surfaces at different installations including walking paths and vehicle travel roads, airfields, decks of naval ships, passageways, etc.

BACKGROUND OF THE INVENTION

The measurement of surface slip resistance is necessary to determine whether a surface is safe for walking of individuals or movement of equipment thereon, so as to prevent accidents for example. Slip meters for such purposes are generally known, such as the tribometer disclosed in U.S. Pat. No. 5,259,236 to English. Such slip meter instruments are designed for manually controlled testing of smooth or textured surfaces, involving manual movement of a slip index gauge, pressure adjustment of a hydraulic type of actuator and change of its air cylinder, and manual recording of slip index number. Furthermore, such prior art slip meters measure surface traction within a rather limited scale range, which often excludes some non-skid surfaces that are worn out. It is therefore an important object of the present invention to provide a slip meter device that is portable and avoids the manual labor intensive tasks heretofore required for operation thereof, as well as to improve operational capability so as to enlarge coverage of surface traction area including worn out non-skid surfaces and otherwise automate slip resistance measurement, as well as to make the slip meter device user friendly.

SUMMARY OF THE INVENTION

Pursuant to the present invention, a slip meter device is provided with a portable frame on which a magnetic type actuator is pivotally mounted for motorized displacement to a preselected angular position at an inclination angle to a test surface when the frame is positioned at the location to be tested. When so positioned, under a battery operated electrical energy source the magnetic actuator is energized to slidably displace a test specimen into contact with the test surface to apply a predetermined linear force to the test specimen through a strain gauge plate. Through one or more load cells mounted on the strain gauge plate under stress of the linear force being transmitted therethrough, strain measurement signals reflecting variations in slip resistance are fed to a computerizing circuit for direct automated output of slip resistance data.

BRIEF DESCRIPTION OF THE DRAWING

A more complete appreciation of the invention and many of its attendant advantages will be readily appreciated as the same becomes better understood by reference to the following detailed description when considered in connection with the accompanying drawing wherein:

FIG. 5 is a top partial view taken substantially through a plane indicated by section line 5—5 in FIG. 4;

FIG. 6 is a diagrammatic presentation of the device illustrated in FIGS. 1–5 and the circuitry associated therewith;

FIG. 7 is a top partial view corresponding to that of FIG. 5, illustrating another embodiment;

FIG. 8 is a simplified circuit diagram corresponding to the arrangement illustrated in FIG. 7; and FIG. 9 is a graphical diagram operationally related to the arrangement illustrated in FIGS. 7 and 8.

DETAILED DESCRIPTION OF THE PREFERRED EMBODIMENTS

Figure 1:
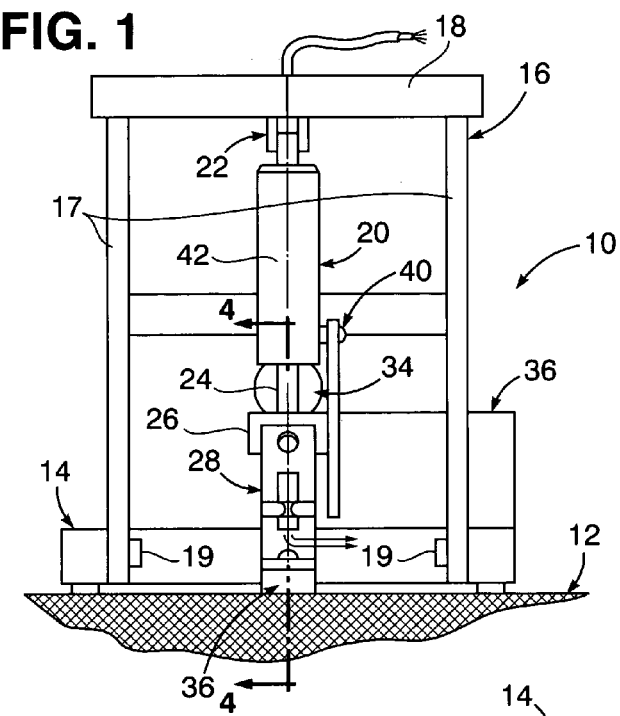
FIG. 1 is a front elevation view of a slip resistance measuring device constructed in accordance with the present invention, positioned on a test surface.
Figure 2:
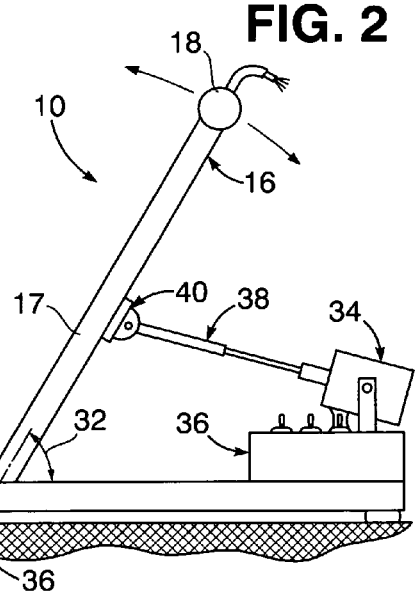
FIG. 2 is a side elevation view of the slip resistance measuring device illustrated in FIG. 1.
Figure 3:
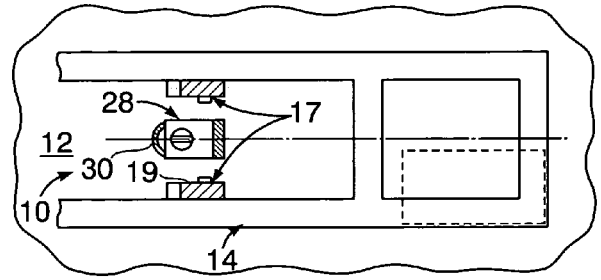
FIG. 3 is a top section view taken substantially through a plane indicated by section line 3—3 in FIG. 2.
Figure 4:
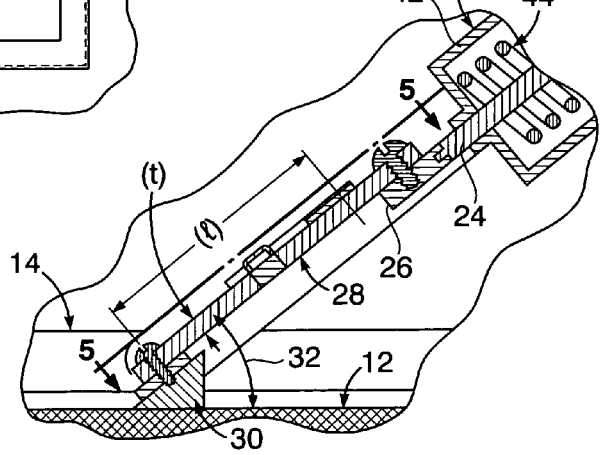
FIG. 4 is a partial side section view taken substantially through a plane indicated by section line 4—4 in FIG. 1.

Referring now to the drawings in detail, FIGS. 1–3 illustrate a tribometer type of portable slip resistance measuring device 10 disposed on a surface 12 to be tested. The slip resistance measuring device 10 embodies a generally rectangular frame 14 through which various components of the device 10 are supported on the test surface 12, including an angularly positioned mast assembly 16 having a pair of mast arms 17 pivotally connected at their lower ends by hinges 19 to the frame 14, and a cross-beam 18 interconnecting the upper ends of the mast arms 17. An axially elongated magnetic actuator 20 is pivotally suspended by a hinge 22 at its upper end from the cross-beam 18 midway between the mast arms 17 as shown in FIG. 1. Projecting from the lower end of the magnetic actuator 20 is an actuator rod 24 connected through an attachment plate 26 to a strain gauge plate 28 having a test specimen 30 attached thereto adjacent its lower end as shown in FIGS. 1, 2 and 4. The strain gauge plate 28 is angularly positioned over the test surface 12 at a predetermined inclination angle (32) thereto as designated in FIGS. 2 and 4 by angular displacement of the mast arms 17 about the hinges 19 on the frame 14. Such angular positioning of the mast arms 17 and the magnetic actuator 20 with the strain gauge plate 28 is effected by means of an electric position adjustment motor 34 pivotally mounted on the frame 14 by a housing 36, as shown in FIGS. 1 and 2. The housing 36 encloses control circuitry associated with the motor 34 as hereinafter described for pivotal displacement of the mast arms 17 through an actuator rod 38 extending from the motor 34 and pivotally connected to the mast arms 17 and to the magnetic actuator 20 by a hinge bracket 40.

According to another embodiment of the present invention as sown in FIG. 7, the strain plate 28 hereinbefore described is replaced by a strain plate 54, which is provided with two load cells 56a and 56b mounted thereon, spaced apart by a distance (l) for measurement of strain therebetween. The load cells 56a and 56b are connected to three terminals 58, 60 and 62 as shown in FIG. 7 and electrically diagrammed in FIG. 8. FIG. 9 graphically diagrams variations in slip resistance as a function of the changing strain (e) produced in the strain plate 54 and the spacings between the test specimen 30 and the load cells 56a and 56b connected through the signal terminals 58, 60 and 62 to the automated circuitry 52 as diagrammed in FIG. 6 through which measurement of the slip resistance of the surface 12 is effected.

As a result of the foregoing description of the portable slip resistance measuring device 10, the static and kinetic slip resisting friction of the surface 12, such as that of a non-skid deck, may be readily determined automatically by one person without manual data recordation.

Obviously, other modifications and variations of the present invention may be possible in light of the foregoing teachings. It is therefore to be understood that within the scope of the appended claims the invention may be practiced otherwise than as specifically described.

What is claimed is:

1. A slip meter for measurement of surface slip resistance between a test specimen and a test surface, comprising: self-energized magnetic means for generating a linear force; positioning means on which the magnetic means is mounted for establishing contact of the test specimen with the test surface at an angle of incidence while said linear force is transmitted from the magnetic means to the test surface through the test specimen; and load sensing means connected to the test specimen for collecting and recording measurement data in response to said contact established between the test specimen and the test surface corresponding to said surface slip resistance.

2. The slip meter as defined in claim 1, wherein said magnetic means comprises: a force exerting actuator rod pivotally interconnected between the positioning means and the test specimen; a magnetic coil through which the actuator rod extends; an electric power supplying battery; and switch means interconnecting the battery with the magnetic coil for exerting said linear force on the actuator rod applied to the test specimen.

3. The slip meter as defined in claim 2, wherein said test specimen comprises:

an anchored strain arm displaced into engagement with the test surface by the actuator rod; and load cell means mounted on the strain arm and connected to the load sensing means for transmission of load sensing signals thereto.

4. The slip meter as defined in claim 1, wherein said test specimen comprises:

an anchored strain arm displaced into engagement with the test surface by the magnetic means;

and load cell means mounted on the strain arm and connected to the load sensing means for transmission of load sensing signals thereto.

* * * * *